(12) United States Patent
Nichols et al.

(10) Patent No.: US 10,078,055 B2
(45) Date of Patent: Sep. 18, 2018

(54) LED STROBE

(71) Applicant: AVID Labs, LLC, Fort Wayne, IN (US)

(72) Inventors: Joel Nichols, Columbia City, IN (US); Alex Tollington, Fort Wayne, IN (US); Adam Brososky, Fort Wayne, IN (US); Veselin Dimitrov, Fort Wayne, IN (US)

(73) Assignee: Avid Labs, LLC, Fort Wayne, IN (US)

( * ) Notice: Subject to any disclaimer, the term of this patent is extended or adjusted under 35 U.S.C. 154(b) by 145 days.

(21) Appl. No.: 15/159,446

(22) Filed: May 19, 2016

(65) Prior Publication Data

US 2016/0341669 A1     Nov. 24, 2016

Related U.S. Application Data

(60) Provisional application No. 62/163,482, filed on May 19, 2015.

(51) Int. Cl.
*H05B 33/08* (2006.01)
*G01N 21/88* (2006.01)

(52) U.S. Cl.
CPC ..... *G01N 21/8806* (2013.01); *H05B 33/0824* (2013.01); *H05B 33/0869* (2013.01); *G01N 2021/8838* (2013.01)

(58) Field of Classification Search
CPC ....... G01N 21/8806; G01N 2021/8838; H05B 33/0842; H05B 33/0824; H05B 33/0869
See application file for complete search history.

(56) References Cited

U.S. PATENT DOCUMENTS

| 6,022,124 | A | * | 2/2000 | Bourn | ............... G01N 21/8806 |
| | | | | | 362/231 |
| 6,362,578 | B1 | | 3/2002 | Swanson et al. | |
| 6,586,890 | B2 | | 7/2003 | Min et al. | |
| 6,798,152 | B2 | | 9/2004 | Rooke et al. | |
| 7,321,203 | B2 | | 1/2008 | Marosek | |
| 7,740,371 | B1 | * | 6/2010 | Lebens | ................... F21L 4/027 |
| | | | | | 315/127 |
| 7,843,146 | B2 | | 11/2010 | Chang Chien et al. | |
| 7,990,081 | B2 | | 8/2011 | Chandran et al. | |
| 8,247,992 | B2 | | 8/2012 | Liu et al. | |
| 8,558,482 | B2 | | 10/2013 | Chu | |
| 8,716,992 | B2 | | 5/2014 | Takano et al. | |
| 2012/0249000 | A1 | | 10/2012 | Kawai et al. | |

(Continued)

FOREIGN PATENT DOCUMENTS

KR     2009026564 A  *  3/2009

*Primary Examiner* — David Harvey
(74) *Attorney, Agent, or Firm* — Taylor IP, P.C.

(57) ABSTRACT

A strobe light system for use with a camera, the strobe light system including an LED light source, a triggering signal input for the reception of a triggering signal, an electrical power source and a control circuit. The control circuit is coupled to the LED light source. The control circuit has a first transistor and a second transistor. The first transistor, the second transistor and the LED are electrically in series with the electrical power source. The first transistor is controlled to establish an electrical power level that is to be conducted through the LED. The second transistor being subject to the triggering signal to thereby electrically conduct for a predetermined amount of time thereby establishing an electrical current pulse through the LED.

17 Claims, 4 Drawing Sheets

(56) References Cited

U.S. PATENT DOCUMENTS

2012/0306586 A1 12/2012 Wan et al.
2013/0266041 A1 10/2013 Giri et al.
2014/0210374 A1 7/2014 Schoel et al.

* cited by examiner

LED STROBE

CROSS REFERENCE TO RELATED APPLICATIONS

This is a non-provisional patent application based on U.S. Provisional Application Ser. No. 62/163,482, entitled "EXTERNAL SYSTEM SYNCHRONIZABLE HIGH-SPEED HIGH-POWER LED STROBE WITH TEMPERATURE DE-RATING PROTECTION AND ADJUSTABLE POWER OUTPUT, filed May 19, 2015 which is incorporated herein by reference.

BACKGROUND OF THE INVENTION

1. Field of the Invention

The present invention relates to strobe light systems and more particularly to an LED strobe light used by with an imaging device.

2. Description of the Related Art

In the field of image inspection of moving objects a strobe light or stroboscopic lamp, commonly called a strobe, is used to produce regular flashes of light to illuminate the moving object, of which an image is made. A typical commercial strobe light has a flash energy in the region of 10 to 150 joules, and discharge times as short as a few milliseconds, often resulting in a flash power of several kilowatts.

Historically, the light source was often a xenon flash lamp, or flashtube, which has a complex spectrum and a color temperature of approximately 5,600 kelvins. If colored light was desirable, then appropriately colored gels are used to filter the light.

Special calibrated strobe lights, capable of flashing up to hundreds of times per second, are used in industry to stop the appearance of motion of rotating and other repetitively operating machinery and to measure, or adjust, the rotation speeds or cycle times of the equipment. Since this stop is only apparent, a marked point on the rotating body will either appear to move backward or forward, or not move, depending on the frequency of the strobe-flash. If the flash occurs equal to the period of rotation the marked point will appear to not move. Any non-integer flash setting will make the mark appear to move forward or backward, depending on the relative frequency of the strobe light and the rotation of the device.

Linear motion of a test item that is to be inspected requires that an image be formed with a very short shutter speed and/or a very sharply defined light strobe, so that details of the item being inspected can be seen. A problem encountered with prior art LED light strobes is that they have an elongated timeframe in which light is supplied causing the image to be somewhat blurred. Often these LED light strobes use a pulse width modulation to control the duration of the strobed light.

What is needed in the art is an LED strobe system with a sharply defined light pulse.

SUMMARY OF THE INVENTION

The present invention provides a quick switching high power LED strobe light system.

The invention in one form is directed to a strobe light system for use with a camera, the strobe light system including an LED light source, a triggering signal input for the reception of a triggering signal, an electrical power source and a control circuit. The control circuit is coupled to the LED light source. The control circuit has a first transistor and a second transistor. The first transistor, the second transistor and the LED are electrically in series with the electrical power source. The first transistor is controlled to establish an electrical power level that is to be conducted through the LED. The second transistor being subject to the triggering signal to thereby electrically conduct for a predetermined amount of time thereby establishing an electrical current pulse through the LED.

The invention in another form is directed to a camera based inspection system using a strobe light system. The strobe light system including an LED light source, a triggering signal input for the reception of a triggering signal, an electrical power source and a control circuit. The control circuit is coupled to the LED light source. The control circuit has a first transistor and a second transistor. The first transistor, the second transistor and the LED are electrically in series with the electrical power source. The first transistor is controlled to establish an electrical power level that is to be conducted through the LED. The second transistor being subject to the triggering signal to thereby electrically conduct for a predetermined amount of time thereby establishing an electrical current pulse through the LED.

An advantage of the present invention is that a sharply defined light pulse results.

Another advantage of the present invention is that the thermal characteristics of the LED are compensated for during operation.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates embodiment of the invention, in one form, and such exemplification is not to be construed as limiting the scope of the invention in any manner.

DETAILED DESCRIPTION OF THE INVENTION

Figure 1:
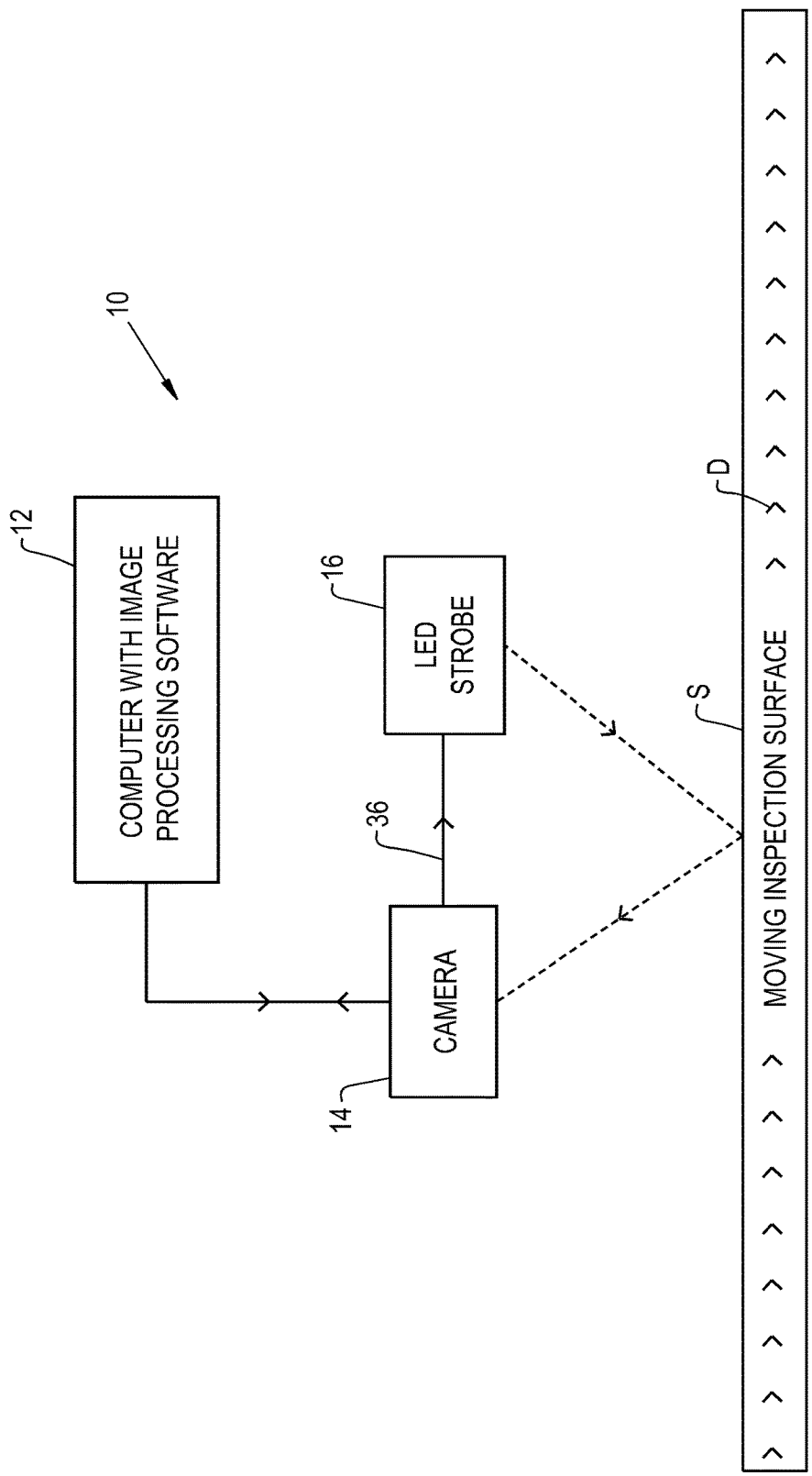
FIG. 1 is a schematical block diagram overview of an inspection system using an embodiment of a LED strobe light system of the present invention.

Referring now to the drawings, and more particularly to FIG. 1, there is shown an inspection system 10 including a computer 12, a camera 14 and an LED strobe light system 16. As surface S moves in direction D computer 12 initiates an operation of camera 14, which may be a programed operation of camera 14, or the initiation of each image may originate in computer 12. The rate at which the inspection is preformed can be tied to a speed sensor that detects the speed in which surface S is moving.

Light from LED strobe light system 16 is directed to surface S and camera 14 receives the light and creates an image of the surface S that is illuminated. The illumination is in the form of a light pulse and camera 12 can be configured to have a shutter to control the duration of an image forming time. However, the duration of the light pulse from LED strobe light system 16 can effectively serve as the shutter, which serves to give an image of surface S at a particular small area along surface S for a moment in time. Repeated flashes of LED strobe light system 16 provide multiple images for analysis by computer 12.

Figure 2:
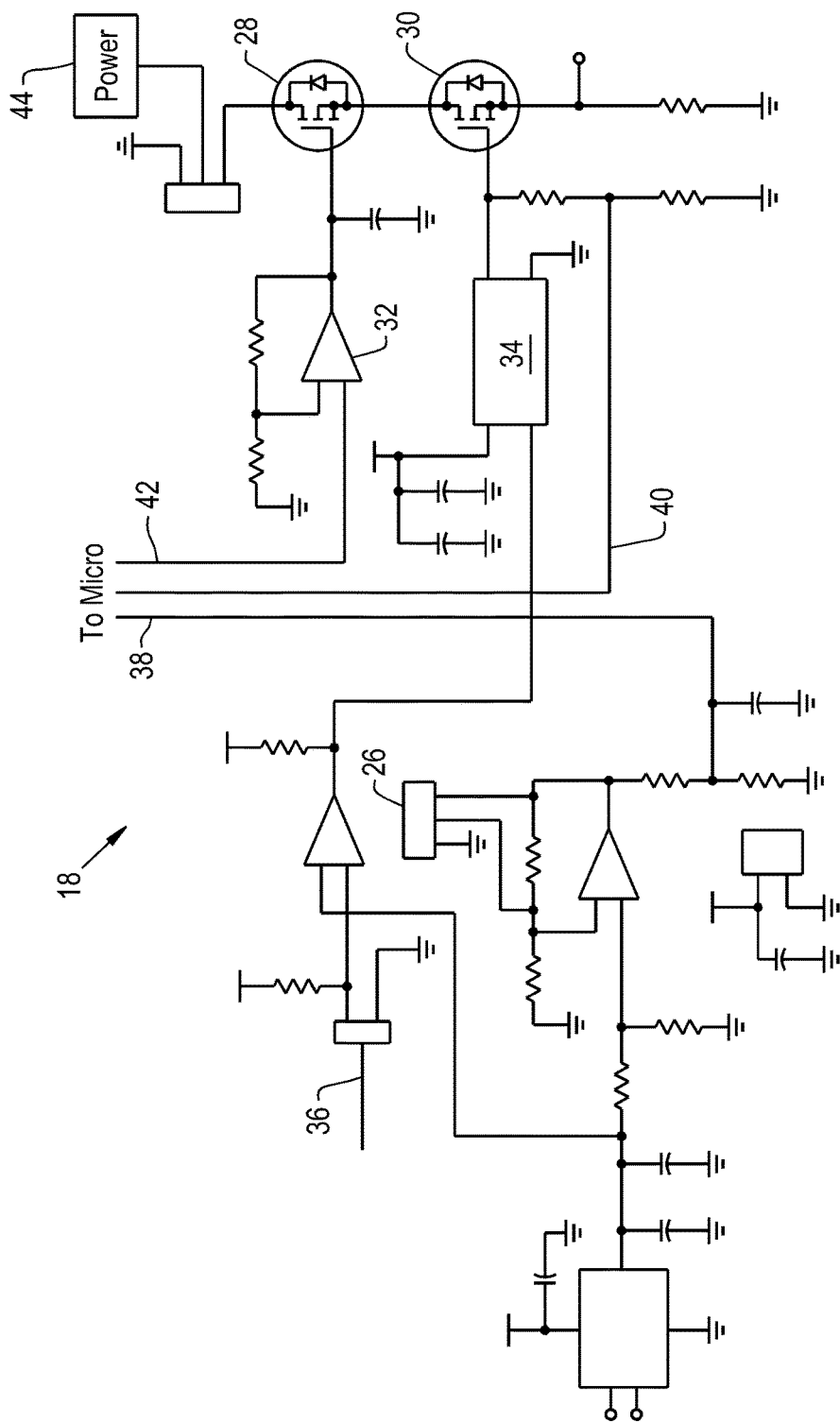
FIG. 2 is an electrical schematic of elements the strobe light system of FIG. 1.
Figure 3:
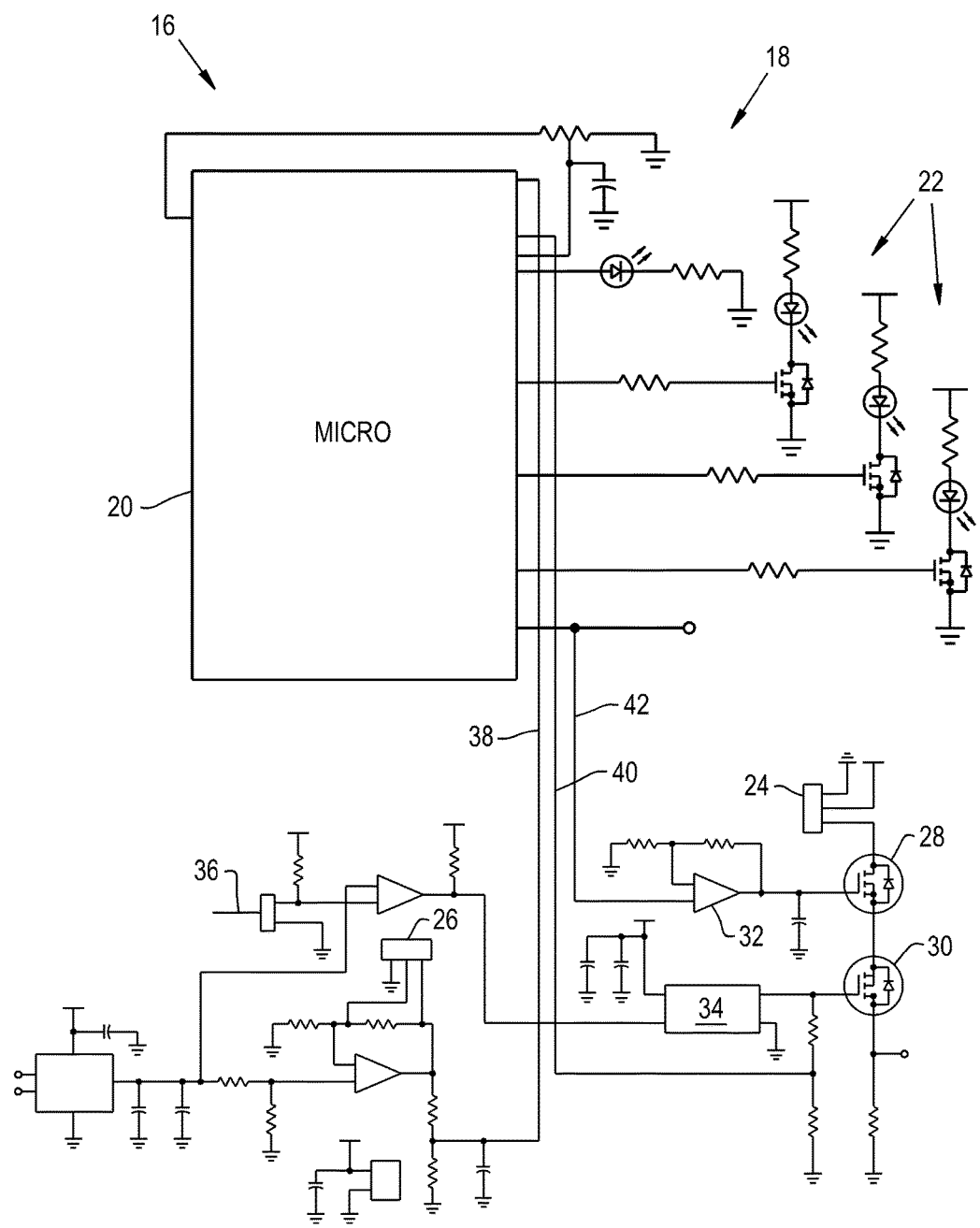
FIG. 3 is another electrical schematic that incorporates the schematic of FIG. 2.

Now, additionally referring to FIGS. 2 and 3 there is illustrated a control circuit 18, which is part of LED strobe light system 16. Control circuit 18 has a microprocessor 20, status indicators 22, an LED 24, a thermistor 26, transistors 28 and 30, amplifiers 32 and 34, a triggering input 36, signal lines 38, 40 and 42, and a power source 44. FIG. 2 is an enlarged section of the circuit 18 shown in FIG. 3.

LED 24 supplies the light when triggering input 36 receives a signal from camera 14. This is accomplished under the control of microprocessor 20. Thermistor 26 is a temperature sensing device 26 that is in thermal contact with LED 24 and provides a thermal signal on line 38 to microprocessor 20. When the triggering event occurs on input 36 the signal is sent to amplifier 34 that triggers transistor 30 to conduct by supplying voltage to the gate input of transistor 30 for a predetermined amount of time and then the voltage is removed by amplifier 34. When the voltage signal arrives on the gate input of transistor 30 a reduced voltage level is supplied to line 40 that is detected by microprocessor 20 for further processing. The level of current that is selected to flow through LED 24 is selected by way of a voltage level applied to the gate of transistor 28, since the voltage level adjusts the conductance value of transistor 28. The series arrangement of transistors 28 and 30 with LED 24 and power source 44 allow one transistor to exclusively deal with the firing time of LED 24 and the other transistor to deal with the current level. The voltage level on the gate terminal of transistor 28 is supplied by amplifier 32 as a result of the input supplied on line 42 from microprocessor 20.

Transistors 28 and 30 are field effect transistors (FET) with their conductance being a function of voltage applied to the gate terminals. Here, advantageously transistor 28 is used to establish the amount of current that will flow through LED 24 by establishing the conductance of the series circuit. Meanwhile transistor 30 is used to trigger the current flow through LED 24 and transistor 28. This allows transistor 30 to be rapidly turned off and control the light output from LED 24. LED 24 itself may be composed of communication type diodes.

Thermistor 26 reacts to rising temperature in LED 24 and varies the signal level on line 38 to thereby allow microprocessor 20 to then alter the current level through LED 24 by altering the voltage on the gate terminal of FET 28.

Figure 4:
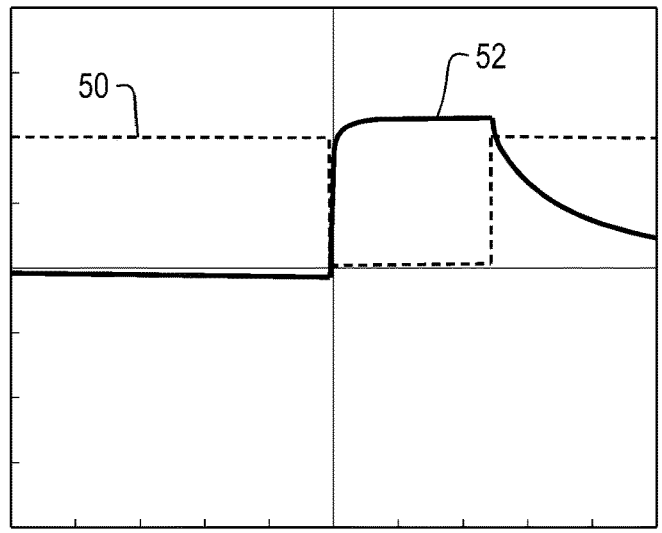
FIG. 4 is a depiction of the response of the LED strobe light of a prior art system.
Figure 5:
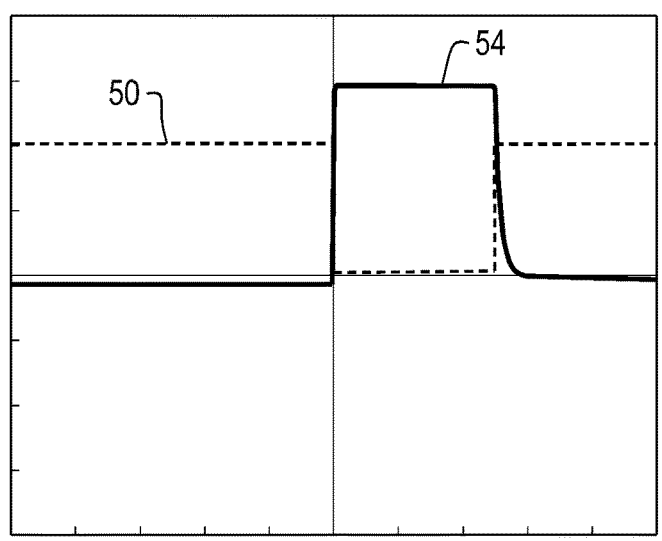
FIG. 5 is a depiction of the response of the LED strobe light system of the present invention.

Now, additionally referring to FIGS. 4 and 5 there are shown results of tests done with a prior art system illustrated in FIG. 4 and the same test performed with the current invention in FIG. 5. Triggering signal 50 in each case is the same duration and value of voltage change. The response 52 in the form of light output of the prior art has an elongated shutdown time, which may be caused by several shortcomings in the controlling electronics, which may or may not use a pulse width modulation system. As can be seen in FIG. 5 the light output energy is expended much closer to the triggering signal with very little output after the triggering pulse. An advantage of the present invention is that the light does not linger, so that a blurring of the image is obviated or at least significantly reduced.

The present invention incorporates temperature de-rating with an adjustable power output. The circuit thus removes the need for Pulse Width Modulated dimming of the prior art. Circuit 18 is used to control the power output to LED 24. The circuit design has been developed to control the current supply to LED 24. LED strove light system 16 is used in conjunction with camera 14 to take high speed photos. The system is designed for varying frame rates and varying duty cycles. The system 10 works at least from 10 Hz to 240 Hz with duty cycles of 1%-10%, however these figures will vary as camera technology increase in speed. The circuit is designed to account for future speed increases of improved cameras 14 and changes in the duty cycle. It is anticipated that from 1 to 5,000 frames per second and duty cycles of up to 50% are within the capability of the inventive circuit 18.

For temperature feedback the current could not be controlled with traditional PWM dimming techniques as this would affect the image taken by camera 14 so a current sense feature has been incorporated into circuit 18.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A strobe light system for use with a camera, the strobe light system comprising:
    an LED light source;
    a triggering signal input for the reception of a triggering signal;
    an electrical power source; and
    a control circuit coupled to the LED light source, the control circuit including:
        a first transistor;
        a second transistor, the first transistor, the second transistor and the LED are electrically in series with the electrical power source, the first transistor being controlled to establish an electrical power level that is to be conducted through the LED, the second transistor being subject to the triggering signal to thereby electrically conduct for a predetermined amount of time thereby establishing an electrical current pulse through the LED; and
        a temperature sensing device in thermal contact with the LED, the temperature sensing device providing a temperature signal representative of a temperature of the LED, the temperature signal influencing the control of the first transistor.

2. The strobe light system of claim 1, wherein the first transistor and the second transistor are both Field Effect Transistors (FET).

3. A strobe light system for use with a camera, the strobe light system comprising:
    an LED light source;
    a triggering signal input for the reception of a triggering signal;
    an electrical power source; and
    a control circuit coupled to the LED light source, the control circuit including:

a first transistor; and
a second transistor, the first transistor, the second transistor and the LED are electrically in series with the electrical power source, the first transistor being controlled to establish an electrical power level that is to be conducted through the LED, the second transistor being subject to the triggering signal to thereby electrically conduct for a predetermined amount of time thereby establishing an electrical current pulse through the LED, the first transistor and the second transistor are both Field Effect Transistors (FET);
a first amplifier circuit driving the first transistor; and
a second amplifier circuit driving the second transistor, the first amplifier providing a voltage level to the first transistor to establish the electrical power level, the second amplifier providing an electrical voltage signal to a gate terminal of the second transistor for the predetermined amount of time and removing the voltage signal from the gate terminal immediately after the predetermined time.

4. The strobe light system of claim 3, wherein the voltage level supplied to the first transistor by the first amplifier is varied to diminish electrical current through the first transistor and hence the current through the LED referred to as current dimming of the LED.

5. The strobe light system of claim 4, wherein the current dimming of the LED takes place proximate to an end of the predetermined time.

6. The strobe light system of claim 5, wherein the current dimming of the LED takes place after the end of the predetermined time.

7. The strobe light system of claim 1, wherein the temperature sensing device is a thermistor.

8. The strobe light system of claim 1, wherein the level of the temperature of the LED represented by the temperature signal alters the amount of current allowed through the LED during the predetermined amount of time.

9. The strobe light system of claim 1, wherein the camera is electrically coupled to the triggering signal input.

10. An inspection imaging system, comprising:
a camera; and a strobe light system synchronized to the camera, the strobe light system including:
an LED light source;
a triggering signal input for the reception of a triggering signal;
an electrical power source; and
a control circuit coupled to the LED light source, the control circuit including:
a first transistor;
a second transistor, the first transistor, the second transistor and the LED are electrically in series with the electrical power source, the first transistor being controlled to establish an electrical power level that is to be conducted through the LED, the second transistor being subject to the triggering signal to thereby electrically conduct for a predetermined amount of time thereby establishing an electrical current pulse through the LED, the first transistor and the second transistor are both Field Effect Transistors (FET);
a first amplifier circuit driving the first transistor; and
a second amplifier circuit driving the second transistor, the first amplifier providing a voltage level to the first transistor to establish the electrical power level, the second amplifier providing an electrical voltage signal to a gate terminal of the second transistor for the predetermined amount of time and removing the voltage signal from the gate terminal immediately after the predetermined time.

11. The inspection imaging system of claim 10, wherein the voltage level supplied to the first transistor by the first amplifier is varied to diminish electrical current through the first transistor and hence the current through the LED referred to as current dimming of the LED.

12. The inspection imaging system of claim 11, wherein the current dimming of the LED takes place proximate to an end of the predetermined time.

13. The inspection imaging system of claim 12, wherein the current dimming of the LED takes place after the end of the predetermined time.

14. The inspection imaging system of claim 10, wherein the control circuit further includes a temperature sensing device in thermal contact with the LED, the temperature sensing device providing a temperature signal representative of a temperature of the LED, the temperature signal influencing the control of the first transistor.

15. The inspection imaging system of claim 14, wherein the temperature sensing device is a thermistor.

16. The inspection imaging system of claim 14, wherein the level of the temperature of the LED represented by the temperature signal alters the amount of current allowed through the LED during the predetermined amount of time.

17. The inspection imaging system of claim 10, wherein the camera is electrically coupled to the triggering signal input.

* * * * *